(12) United States Patent
Berkson et al.

(10) Patent No.: US 8,492,435 B2
(45) Date of Patent: *Jul. 23, 2013

(54) COMPOSITION FOR TREATING A DERMAL ANOMALY

(76) Inventors: Lindsey Berkson, Austin, TX (US); Kenneth G. Burton, Sunrise Beach, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 12/765,361

(22) Filed: Apr. 22, 2010

(65) Prior Publication Data

US 2010/0210728 A1    Aug. 19, 2010

Related U.S. Application Data

(63) Continuation of application No. 10/992,623, filed on Nov. 17, 2004, now Pat. No. 7,731,993.

(51) Int. Cl.
*A61K 31/21*     (2006.01)

(52) U.S. Cl.
USPC ............................................... 514/509

(58) Field of Classification Search
USPC ................................................ 514/509
See application file for complete search history.

(56) References Cited

U.S. PATENT DOCUMENTS

| 5,543,430 | A * | 8/1996 | Kaesemeyer | 514/565 |
|---|---|---|---|---|
| 6,194,455 | B1 * | 2/2001 | Wharton | 514/532 |
| 6,287,601 | B1 * | 9/2001 | Russell | 424/485 |
| 6,883,466 | B1 * | 4/2005 | Chambers | 119/850 |
| 2003/0026849 | A1 * | 2/2003 | Thomas | 424/608 |
| 2003/0104033 | A1 * | 6/2003 | Lai et al. | 424/439 |
| 2004/0047919 | A1 * | 3/2004 | Srivastava et al. | 424/718 |
| 2005/0075391 | A1 * | 4/2005 | Gorfine | 514/509 |

OTHER PUBLICATIONS

Kimball, V.G., DVM: Veterinary State Board Questions and Answers; Second Ed., 1914, The Washington Square Press, Philadelphia, PA, p. 253.*

* cited by examiner

*Primary Examiner* — Patricia Leith
(74) *Attorney, Agent, or Firm* — Patton Boggs LLP

(57) ABSTRACT

An improved composition for treatment of ulcer-type skin conditions. The composition is primarily characterized by a combination of nitroglycerin and arginine. Other embodiments comprise emollient cream, mineral oil, tumeric powder, folic acid, vitamin B12, and zinc citrate. The composition is particularly effective in improving blood flow in the underlying capillary bed about the wound, improving nerve growth about the wound, increasing circulation, and having a standardized and more predictable therapeutic characteristic.

23 Claims, No Drawings

COMPOSITION FOR TREATING A DERMAL ANOMALY

CROSS-REFERENCED TO RELATED APPLICATIONS

This application is a Continuation of U.S. patent application Ser. No. 10/992,632, filed Nov. 17, 2004, currently pending. The contents of which are incorporated herein by reference in its entirety.

BACKGROUND OF THE INVENTION

1. Field of the Invention

The present invention generally relates to an improved composition for treatment of a skin condition. More specifically, the present invention relates to an improved composition for treatment for common types of skin ulcers, including diabetic, stasis, and decubitus ulcers.

2. Background Information

Various treatments for ulcer-type skin conditions are known in the art. More specifically, skin ulcer treatment regimens heretofore devised and utilized are known to consist basically of familiar, expected and obvious structural configurations, notwithstanding the designs encompassed by the prior art which have been developed for the fulfillment of various objectives and requirements.

Known documents include: U.S. Pat. No. 6,569,840, which relies on modified (oxidized) heparins; and U.S. Pat. No. 5,789,439, which relies one pharmaceutical use of forskolin derivatives.

While these treatments may fulfill their respective, particularly claimed objectives and requirements, the aforementioned documents do not disclose an improved composition for treating skin ulcers such as Applicant's present invention.

Today's society, particularly in the United States, is increasingly susceptible to Diabetes. In fact, the incidence of diabetes is rising precipitously. Genetic traits, in combination with poor diet and lack of exercise, are thought to be significant factors in one's likelihood of coming down with diabetes.

Type II diabetes is the most common form of the disease and accounts for 90 to 95 percent of all diabetes. Throughout the world, the incidence of Type II diabetes is nearing epidemic proportions. Examination of current and expected diabetic trends (and the detrimental effects therefrom) is helpful for grasping the tremendous need for the present invention.

By way of example, the Center for Disease Control and Prevention ("CDC") reports an increase in the cases of diagnosed adult diabetes of 49% between 1990 and 2000. Further, the CDC estimates the diabetes, both diagnosed and undiagnosed, affects approximately seventeen million Americans (or some 6.2% of the U.S. population).

Diabetes is a prevalent disease and an ever-growing domestic and international public health concern. The World Health organization estimates that approximately 150 million people are affected by diabetes; and, these numbers are expected to only get worse (estimated 215 million people affected by 2010; estimated 300 million people affected by 2025). Worldwide, diabetes has a relatively high mortality rate. Diabetes is reportedly among the top five causes of death by disease in most countries, though this may be a conservative ranking. More likely, diabetes is even more deadly as it is frequently under reported on death certificates. Finally, diabetes does not discriminate. Similar trends in the increase incidence of diabetes has been observed across both sexes, virtually every age group, different ethic groups, all socio-economic backgrounds, and every state in the Union. Importantly, the occurrence of diabetes and skin ulcers is directly related. Accordingly, the sharp increase in the number of people having diabetes has led to an increase in the number of people affected by skin ulcers. By way of example, diabetics have a fifteen percent chance of developing a foot ulcer during their lifetime. Of those diabetics that develop foot ulcers, approximately twenty percent will require amputation. (International J of Pharm Compounding 8(4) July/August 2004, 269). Such amputations are also increasing at an alarming rate. Between 1990 and 2000, the number of amputations resulting from foot ulcers increased by twenty six percent. This trend is expected not only to continue, but to worsen in the coming years. Foot ulcers cause approximately eighty five percent of all diabetic amputation of the lower extremities (Emergency Medicine 36(8) Au 2004, 14-23). The number of such lower extremity amputations (LEA's) now exceeds 100,000 per year!

Recurring foot ulcers, and the amputations that may result, present a continuing problem on a national and global scale. In the event that an ulcer is successfully treated, it is more likely than not that the ulcer will reoccur. Recurrence rates associated with diabetic foot ulcers and resulting LEA's are commonly as high as fifty percent to seventy percent over a period of three to five years.

Those skilled in the art of ulcer treatment realize that the accepted standard of care is simply not working. Current medications s of treatment all too commonly fail to heal ulcers and prevent the occurrence of complications such as infection and gangrene. Overall, fifty to eighty percent of patients having diabetic foot ulcers will heal within six months, assuming optimal management from a multi-disciplinary team. (Emergency Medicine 36(8) August, 2004, 14-23). However, all too common complications require hospitalization, painful and expensive surgery, and a prolonged rehabilitation regimen. With the incidence of ulcer recurrence as high as seventy percent, the healing of one ulcer is often rapidly followed by the development of a new one.

In view of the serious consequences of diabetic ulcers and the utter inability to effectively treat those ulcers, a great need exists for an improved treatment. Applicant's invention, through a novel composition and associated methods of applying that composition, provides a much needed solution to the problems mentioned above. While known regimens rely on the use of debridement and washing, the present invention does away with this accepted treatment. Applicant has found that such treatment typically results in scarring, non-closure of the wound, and/or recurrence. Instead, the present invention relies on a novel combination of ingredients that is particularly effective in increasing blood flow and nerve growth about the wound.

A few practical examples, experienced first hand by Applicant, shed light on the startling results associated with the present invention:

Patient B has had diabetes for several years, the last two of which he has been confined to a wheel chair. During this past year Patient B has been hospitalized for non-healing pressure ulcers on his buttock region. Every developed ulcer has caused a tremendous amount of pain an suffering. Also, these ulcers have necessitated surgery and costly medical bills. Complication of these ulcers extended to the pelvic bone, which required removal of a portion of the bone. The present composition was applied to the wound one time per day for a period of three days. By the third day of treatment the wound had decreased in size by approximately twenty five percent. Also, the wound was radically improved, where approximately thirty percent of the wound had been covered with new white granular tissue with obvious healing occurring throughout the entire ulcer. During the next three days, the composition was applied twice daily. After a total of six days of treatment, the original wound was virtually covered with new tissue growth.

Before application of the present composition, Patient F had lost one finger tip to an ulcer and poor circulation. Her entire hand was rigid and swollen. Before treatment, several of Patient F's fingers were at risk of amputation. After a week of application of the present composition, her hand was soft and mobile, had better circulation, less pain, and a reduction of dark areas marked by poor blood flow. A single lesion had been open to the bone; however, after three days of treatment the lesion went from oozing blood and pus to being completely closed. According to standard treatment protocols, Patient F's lesion would have been reopened for further drainage. However, the present regimens avoids such a necessity.

Patient F has an open scalp lesion of approximately two centimeters in length. After three days of treatment (where the patient continued to wash the wound against Applicant's advise), the lesion had decreased by seventy percent. From the fourth to sixth day, the patient did not wash the wound. By the night of the forth day the lesion has completely closed, By day six, the patient reported a fifty percent reduction in pain such that she could rest her head upon a pillow to sleep.

Patient K had a developing lesion between her buttocks, which appeared to have a monilial infection. Applicant fear the overlying yeast infection would block entry of the present composition. After two days of treatment, the lesion had improved by some fifty percent. After a week of treatment, the lesion had completely healed and the patient reported a tremendous decrease in pain and overall discomfort.

SUMMARY OF THE INVENTION

The general purpose of the present invention, which will be described subsequently in greater detail, is to provide an improved composition for the treatment of ulcer-type skin conditions which has many of the advantages of such regimens known in the art and many novel features that result in a new composition of treatment which are not anticipated, rendered obvious, suggested, or even implied by any of the known compositions or methods of treatment, either alone or in any combination thereof.

In view of the foregoing, it is an object of the present invention to provide an improved composition for treatment for ulcer-type skin conditions that does not include substantial debridement.

It is another object of the present invention to provide an improved composition for treatment for ulcer-type skin conditions that does not include substantial washing.

It is another object of the present invention to provide an improved composition for treatment for ulcer-type skin conditions that creates effective vasodilation of underlying capillary beds in patients.

It is another object of the present invention to provide an improved composition for treatment for ulcer-type skin conditions that has a particularly high anti-fungal property.

It is another object of the present invention to provide an improved composition for treatment for ulcer-type skin conditions that increases blood flow to nerves.

It is another object of the present invention to provide an improved composition for treatment for ulcer-type skin conditions that increases nerve growth.

It is another object of the present invention to provide an improved composition for treatment for ulcer-type skin conditions that has a particularly high absorption characteristic.

It is another object of the present invention to provide an improved composition for treatment for ulcer-type skin conditions that is particularly effective in increasing circulation.

It is another object of the present invention to provide an improved composition for treatment for ulcer-type skin conditions that has a particularly effective and standardized distribution characteristic.

It is yet another object of the present invention to provide an improved composition for treatment for ulcer-type skin conditions that incorporates simultaneous application of Arginine and Nitroglycerin.

In satisfaction of these and other related objectives, the present invention provides an improved composition for the treatment of ulcer-type skin conditions. The present invention, by way of a novel composition and associated methods of applying that composition, yields results that simply are not possible with any other known treatments.

The composition of the present invention comprises nitroglycerin and arginine, which have been found to work synergistically to increase the absorption and distribution the other. The combination of these two components has a synergetic effect where each increases circulation and distribution of the other. With simultaneous application of one, the beneficial action of the other is increased. The distribution of each component within the affected tissue is increased with this manner of application. In fact, Applicant has found that such combination results in an approximate fifty percent increase with respect to predictability, distribution about the sound, and standardized action.

In its most preferred form, the present composition comprises: nitroglycerin 2% ointment, emollient cream base, lidocaine (USP powder 99.95), mineral oil (light 65-75 VIS liquid), Tumeric Powder, Folic Acid Dilution (50 MG=2.5 MG FOLI powder), Vitamin B 12 dilution (50 M G=2. 5 M G B 12 powder), Aloe Vera (freeze dried 200:1 powder), Zinc Citrate (Purified Powder), and Arginine (L) (HCL powder). This composition is formed as the triturate powders and wet powders are combined with the mineral oil and then thoroughly mixed with emollient cream. The ingredients are then QS'ed to the desired volume.

Associated application of the present composition are generally characterized by the topical or injectable application of the aforementioned composition. When injected, the medication is typically delivered by syringe in amount depending on the size and depth of the particular lesion. Generally, syringes between ½ ACC and 2 CC are sufficient.

The treatment protocol essentially involves leaving the wound alone to heal on its own. That is, the wound is not to be interfered with and use of anti-bacterial or antimicrobial soaps is to be avoided. Debridement and washing of the wound are to be avoided (such has been discovered to promote scarring, non closure, and recurrence of the ulcer). After application of the composition, the wound is typically covered with a tefla pad (or some equivalent) and breathable tape. This allows the wound to remain fairly dry (substantially free of any undue moisture) and open to the surrounding air.

While the characteristics unique to this treatment protocol may appear to be subtle distinctions at first glance, these distinctions yield a regimen that is different from any such known in the art and produces unexpected (and previously unachievable) results. For instance, the present method increases blood flow to nerves thereby increasing nerve growth. This expedites the growth of new island cells and allows skin to take root and grow. This is a primary reason for the improved results not seen in any of the known treatment regimens. Further, Applicant has devised a compound that creates effective vasodilation of the underlying capillary bed in patients with compromised vascular function The present invention eliminates the need for debridement while acting as an anti-fungal.

DETAILED DESCRIPTION OF THE INVENTION

In the preferred embodiment of the present medicament, and in the medicament upon which an associated method of treatment is based, the primary active ingredients are Nitroglycerin and Arginine. In this preferred embodiment, the Nitroglycerin is in the form of two percent ointment; and, the arginine is in the form of HCL powder.

The preferred nitroglycerin-arginine based compositions of the present invention may be prepared according to the following disclosure and protocol, with variations appropriate to a desired scale or production as will be apparent to person skilled in the production of pharmaceutical preparations:

A. Constituents of Preferred Embodiment of Composition for Remediation of Dermal Anomalies

| Ingredients | Quantity |
| --- | --- |
| Nitroglycerin 2% ointment | 10 GM |
| Arginine (L) HCL Powder | 10 GM |
| Emollient cream base | 100 GM |
| Lidocaine, USP Powder | 2 GM |
| Mineral Oil, Light 65-75 VIS liquid | 8.33 ML |
| Tumeric Powder | .25 GM |
| Folic Acid Dilution 50 MG = 2.5 MG FOLI powder | .02667 GM |
| Vitamin B12 dilution 50 MG = 2.5 MG Bl2 powder | .02 GM |
| Aloe Vera freeze dried 200:1 powder | .2 GM |
| Zinc Citrate Purified Powder | 2 GM |
| Total: | 124.5 GM |

B. General Mixing: Procedure of Preferred Embodiment of Composition for Remediation of Dermal Anomalies 1. Triturate powders and wet powders with mineral oil and mix thoroughly with emollient cream.
2. QS to desired volume.

The formed composition may then be applied topically or through injection. Typically, the composition is applied between one and three times per day. A treatment period between three and ten days is thought to be sufficient to heal the large majority of treated wounds.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed is:

1. A method of treating a human skin anomaly, comprising topically applying a composition to said human skin anomaly wherein said composition comprises:
   nitroglycerin, and
   arginine; and
   wherein said human skin anomaly is an ulcer, lesion, or wound.

2. The method of claim 1, wherein said human skin anomaly is at least partially covered by a breathable pad after application of said composition.

3. The method of claim 1, wherein said composition further comprises an emollient cream base.

4. The method of claim 1, wherein said composition further comprises lidocaine.

5. The method of claim 1, wherein said composition comprises:
   approximately ten parts nitroglycerin; and
   approximately 100 parts emollient cream base.

6. The method of claim 1, wherein said composition of comprises:
   approximately ten parts arginine; and
   approximately 100 parts emollient cream base.

7. A method of treating a human skin anomaly comprising injecting a composition into said human skin anomaly, wherein said composition comprises:
   nitroglycerin; and
   arginine; and
   wherein said human skin anomaly is an ulcer, lesion, or wound.

8. The method of claim 7 further comprising at least partially covering said human skin anomaly with a breathable pad.

9. The method of claim 7, wherein said composition comprises:
   approximately ten parts nitroglycerin.

10. The method of claim 7, wherein said composition comprises:
    approximately ten parts arginine.

11. The method of claim 1, wherein said method does not include debridement or washing of said human skin anomaly during treatment.

12. The method of claim 7, wherein said method does not include debridement or washing of said human skin anomaly during treatment.

13. The method of claim 1, wherein topically applying said composition to said human skin anomaly occurs between 1 and 3 times per day.

14. The method of claim 13, wherein topically applying said composition to said human skin anomaly occurs 3 times per day.

15. The method of claim 13, wherein topically applying said composition to said human skin anomaly occurs 2 times per day.

16. The method of claim 13, wherein topically applying said composition to said human skin anomaly occurs once per day.

17. The method of claim 13, wherein said topical application continues for 3 to 10 days.

18. The method of claim 7, wherein said injection of said composition to said human skin anomaly occurs between 1 and 3 times per day.

19. The method of claim 18, wherein said injection of said composition to said human skin anomaly occurs 3 times per day.

20. The method of claim 18, wherein said injection of said composition to said human skin anomaly occurs 2 times per day.

21. The method of claim 18, wherein said injection of said composition to said human skin anomaly occurs once per day.

22. The method of claim 18, wherein said injections continue for 3 to 10 days.

23. The method of claim 7, wherein said injection further comprises a volume of between 0.5 to 2 CC of said composition.

* * * * *